(12) United States Patent
Burgess-Cassler et al.

(10) Patent No.: US 9,588,108 B2
(45) Date of Patent: Mar. 7, 2017

(54) APPARATUS FOR SIMULTANEOUS DETECTION OF AMINES AND THIOLS

(71) Applicant: ALT BIOSCIENCE, LLC, Lexington, KY (US)

(72) Inventors: Anthony Burgess-Cassler, Lexington, KY (US); George David McClure, Jr., Lexington, KY (US)

(73) Assignee: ALT BIOSCIENCE, LLC., Lexington, KY (US)

( * ) Notice: Subject to any disclaimer, the term of this patent is extended or adjusted under 35 U.S.C. 154(b) by 0 days.

(21) Appl. No.: 14/893,910

(22) PCT Filed: May 22, 2014

(86) PCT No.: PCT/US2014/039210
§ 371 (c)(1),
(2) Date: Nov. 24, 2015

(87) PCT Pub. No.: WO2014/193737
PCT Pub. Date: Dec. 4, 2014

(65) Prior Publication Data
US 2016/0109433 A1    Apr. 21, 2016

Related U.S. Application Data

(60) Provisional application No. 61/956,053, filed on May 30, 2013.

(51) Int. Cl.
*G01N 33/52* (2006.01)
*G01N 21/78* (2006.01)
*G01N 21/77* (2006.01)

(52) U.S. Cl.
CPC .......... *G01N 33/523* (2013.01); *G01N 21/78* (2013.01); *G01N 33/52* (2013.01); *G01N 2021/7759* (2013.01); *G01N 2800/18* (2013.01)

(58) Field of Classification Search
CPC combination set(s) only.
See application file for complete search history.

(56) References Cited

U.S. PATENT DOCUMENTS

| | | | |
|---|---|---|---|
| 4,769,467 A | 9/1988 | Kazuhiro | |
| 2006/0292652 A1* | 12/2006 | Curtis | C12Q 1/48 435/15 |
| 2009/0311142 A1* | 12/2009 | Burgess-Cassler | G01N 33/523 422/400 |
| 2010/0291699 A1 | 11/2010 | Pendergrass et al. | |

OTHER PUBLICATIONS

Patent Cooperation Treaty, International Searching Authority, Search Report and Written Opinion for PCT/US2014/39210, 9 pages, Sep. 10, 2014.

* cited by examiner

*Primary Examiner* — Paul Hyun
(74) *Attorney, Agent, or Firm* — Viksnins Harris & Padys PLLP

(57) ABSTRACT

Disclosed is an apparatus for simultaneous detection of amines and thiols.

3 Claims, 3 Drawing Sheets

APPARATUS FOR SIMULTANEOUS DETECTION OF AMINES AND THIOLS

RELATED APPLICATIONS

This application claims priority to U.S. Provisional Patent Application No. 61/956,053 filed May 30, 2013, the entirety of which is incorporated herein by reference.

FIELD OF THE INVENTION

The field relates to an apparatus for simultaneous detection of amines and thiols.

BACKGROUND OF TRE INVENTION

There is a long-felt need for an apparatus for simultaneous detection of amines and thiols. In particular, the progress of various pathophysiological and/or environmental processes can be monitored through use of such an apparatus, as amines and thiols are produced in increasing abundance as such processes progress.

DESCRIPTION OF THE INVENTION

Figure 1:
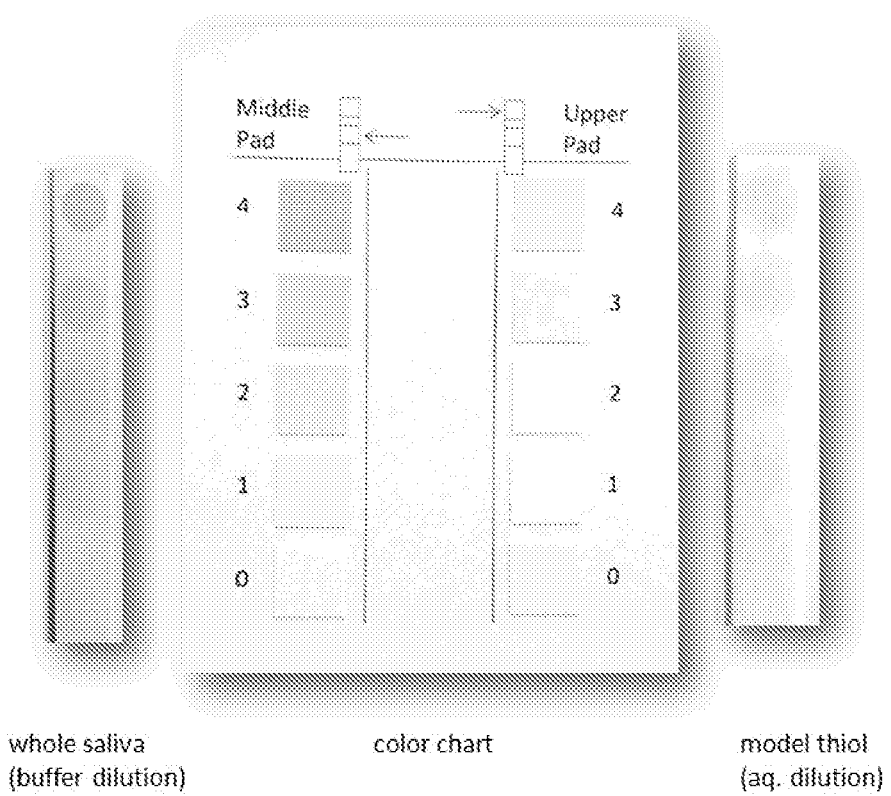
FIG. 1 depicts an example of a color chart such as used for the Prototype 01 test.

An apparatus for simultaneous detection of amines and thiols will be described more fully hereinafter. Such an apparatus may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise. "Or" as in "A or B" is conjunctive, not disjunctive, and accordingly in this instance means at least one member of the set {A, B}.

Phthaldialdehyde (OPA; CAS 643-79-8) is an amine detection compound, used to derivatize amino acids and other primary amines prior to reverse-phase liquid chromatography. Under certain reaction conditions, the derivatized amine compounds produced are fluorescent, and can be detected spectrophotometrically, for example, with excitation at 340 nm and emission at 455 nm. For this purpose, OPA is typically supplied as a basic solution, containing 2-mercaptoethanol. These solutions are sensitive to oxygen and must be kept refrigerated. If allowed to oxidize, they can be reduced, and thereby re-activated, by the addition of 2-mercaptoethanol, to a final level of ~25-30 mM.

OPA reagent immobilized by drying onto a pad matrix containing a non-volatile thiol compound forms fluorescent amine derivatives, but forms brown/gray adducts without added thiol, when hydrated with oral fluid samples collected from various sites. However, visible colors generated with various pure diamines, amino acids and proteins vary considerably, based on the specific compound, the compound's concentration, and the ionic and pH conditions.

5,5'-Dithiobis(2-nitrobenzoic acid) (DTNB; CAS 69-78-3), first described by Ellman, has been used for over 50 years as a biochemical reagent to quantify thiols, such as thiols produced or consumed by enzymatic reactions. It combines with active thiols of numerous types, giving as one of the products a thiolate anion, which exhibits a very high extinction coefficient at ~412 nm.

The thiolate produced upon reaction of DTNB with thiols is intensely yellow, and can be easily quantified by spectrophotometry. It is also possible to use DTNB in dry reagent formulations, to devise semi-quantitative test strips for thiol detection which can be used in conjunction with simple color charts, such as described in US Pat. Pub. No. 20090311142. Such test strips can be used as diagnostic tools to detect/quantify thiols present in bodily fluids. For instance, thiol levels present in oral fluid samples obtained from the gum line of dogs have been found to be directly related to the presence and severity of active periodontal disease and the risk of disease progression. In this instance, there is evidence that the thiols are produced as a result of bacterial infection, which typically underlies such disease.

An apparatus such as is described herein detects amines and thiols. A sample can be applied to multiple pads, each containing a distinct chemistry, or to a single pad containing multiple detection reagents.

For a pad containing OPA or OPA/DTNB, a diagnostic cellulosic paper was a suitable pad matrix. A thicker paper (Ahlstrom #222) was used for the 01 prototype, which had a distinct OPA (OPA-only) pad. This paper was compatible with sample delivered drop-wise to the matrix surface, providing a result with a fairly evenly distributed 'circle' of coloration. A thinner paper (Ahlstrom #319) was used for the 02 prototype, on which pad was immobilized a combined OPA/DTNB reagent, and to which sample was applied by contacting a flocked swab bearing an oral fluid sample with the paper pad. General characteristics of Ahlstrom diagnostic papers ("high purity cotton fibers") can be found at http://www.ahlstrom.com/en/products/fiberComposites/Documents/Liquid%20Filtrati on%20documents/new%/208.5×11liquid%20in%20vitroDiag%20sheet.pdf.

For a pad containing DTNB reagent only (as was the case for the 01 prototype), a suitable matrix was a material such as a Filtrona Transorb material, a non-woven synthetic, e.g., ~0.9 mM thickness. Any of various thicknesses of this material can be selected, depending on the sample volume of the particular format and the backing material employed for the strip. It is possible as well to vary the porosity of this matrix.

Example: pad on which OPA alone was immobilized. Detection reagent, within a mixture of chemicals, was applied to a suitable paper matrix as described herein and dried. The 02 prototype represented a further development of the 01 prototype with regard to the OPA reagent. While used there in combination with a DTNB reagent, OPA can also be used as the sole reagent.

The following recipe is an example of a composition that was prepared to make 100 mL OPA buffer (prepared before the addition of the OPA reagent itself):

| Chemical | ~Concentration In Solution |
| --- | --- |
| 75 mL distilled water | — |
| 3.80 g sodium tetraborate | 1 mM |
| 0.25 mL Tween20 | 0.25%, v/v |
| conc. HCl, added drop-wise, to bring to pH 9.0 | |
| 3.90 g HPβCD | ~26 mM |
| 5 mL methanol | 5%, v/v |

Q.S. to 100 mL with distilled water, filter through 0.2 or 0.45 μm filter, store at room temperature.

A quantity of 3.5 mg OPA per mL of above buffer solution was used to make an OPA solution in which the final OPA concentration was about 26 mM. The resultant mixture was heated (cap not tight) in a 15 mL or 50 mL plastic centrifuge tube, with sequential 3 second bursts in a microwave, capping tightly and mixing gently by inversion after each burst. As the mixture warmed, it became cloudy at around 45-50° C. At this point, the heating was stopped, but mixing of the contents of the closed tube was continued by inversion until the OPA was totally dissolved. As the mixture cooled the cloudiness dissipated and the mixture became clear.

This OPA solution was then applied immediately to a paper matrix on a flat, clean plastic surface until the matrix was saturated. Alternatively, the paper can be dipped into the OPA solution to saturate, then placed on the flat surface. The treated paper is dried in a forced-air dryer for ~1.25-1.75 hr, depending on paper thickness, at ~35-40° C.

Example: pad on which DTNB alone was immobilized. The following recipe is an example of a composition that was prepared to make 600 mL DTNB solution:

| Chemical | ~Concentration (Mm) In Solution |
| --- | --- |
| 400 mL distilled water | — |
| 2.25 g sodium phosphate dibasic (anhydrous) | 100 (total phosphate) |
| 4.55 g sodium phosphate monobasic (dihydrate) | |
| 3.78 g glycerol | 68 |
| 7.5 g myo-inositol | 69 |
| 1.93 g HPβCD | 2.2 |
| 7.5 g sorbitol | 69 |
| 7.5 g trehalose (dihydrate) | 33 |
| 0.15 g DTNB | 0.6 |

Q.S. to 600 mL with distilled water, filter through 0.2 μm filter, store at 2-8° C.

Immobilization onto a pad was undertaken according to methodology such as described in US Pat. Pub. No. 20090311142.

Example: pad on which OPA and DTNB were immobilized. The following procedure was followed: mix 4 parts (by volume) OPA buffer with 1 part (by volume) DTNB solution (final DTNB concentration was ~0.12 mM); add OPA, to give a final concentration of 3.25-3.5 mg/mL (~24-26 mM). Immobilization of the combined reagent mixture onto a pad matrix took place without undue delay.

Immobilization of combined reagent mixture was onto an Ahlstrom paper #319. Another similar paper is also suitable.

Test strips incorporating a pad such as described above were made by affixing a dried treated pad, via an appropriate layer of adhesive, onto a plastic backing such as a plastic backing comprising vinyl, polyester and/or polystyrene, and cutting to width.

Arrangement of Pads in Two-Pad Tests. Pads in two-pad or dual-pad tests can be arranged in various ways, depending on how the test is carried out. In cases where a sample is simply applied sequentially (e.g., drop(s) applied first to one pad, then to the other (like prototype 01)), the pads should be sufficiently close to allow for quick movement of the sample applicator to the second pad, but not so close that there is a risk of cross-contamination, after sample has been applied to each.

In cases involving a folding over of one pad toward another (e.g., sandwiching an applicator between two pads so as to deliver sample to both pads simultaneously), pads need to be sufficiently separated from one another on the backing to allow for the fold-over area, may be similarly sized, and may have their closest adjacent edges aligned, for example, parallel to and equidistant from the fold.

Another series of embodiments each comprises a single pad, where the pad is applied to one end of a test strip, opposite the end of the strip intended to be held by a user.

Examples of Backings for Test Strips. Medical test strips typically are staged upon plastic backings which are white, which is suitable for an embodiment of an apparatus as is described herein. In an embodiment of an apparatus as is described herein, a clear or colored plastic may be selected. A suitable plastic provides a visual contrast when compared to the color and intensity of a test result that develops on the pad or pads. For a simple two-pad test (like prototype 01), white was used, since the visible result colors were different. For a single-pad test (like prototype 02), a blue backing was chosen, since it helped draw the eye to the white pad area, and did not interfere, contrast-wise, with the colored result on that pad.

In cases where a fluorescent product is produced, a suitable backing material would have limited or no inherent fluorescence (some backings may contain whiteners which cause the backing itself to fluoresce).

Examples of Packaging for Test Strips. Since a test is typically activated by wetting one or more pads included in the test with a liquid sample, the test needs to be packaged to protect it from moisture until such time as it is intended that the test be used. In addition, OPA reagent may be subject to oxidation and degradation. Therefore, a foil pouch with low moisture vapor and oxygen transmission rates is suitable, as was used for both prototypes 01 and 02. Such a pouch is generally described at http://wwvv.sorbentsystems.com/spe,cs/pakvf4w.html.

Examples of Color Charts. An example of a color chart such as used for the Prototype 01 test is depicted in FIG. 1.

Figure 2:
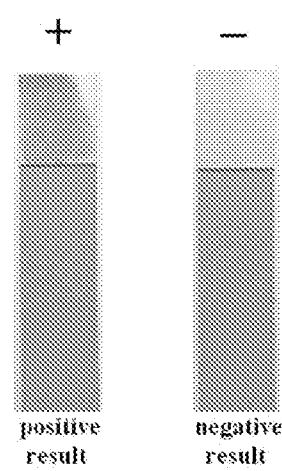
FIG. 2 depicts an example of a color chart such as used for the Prototype 02 test.

An example of a color chart such as used for the Prototype 02 test is depicted in FIG. 2.

Example of Thiol Control. An example of a thiol control such as used for the Prototype 02 test is described below. An example compound which was able be used by a test user as a 'thiol control' (to test that thiol indeed caused the pad to become yellow) was L-cysteine. Another stable thiol compound may provide a suitable control. One embodiment comprised two plastic 1.5 mL microfuge tubes, one containing ~8 mg L-cysteine, and the other 1 mL of distilled water. A user was instructed to carefully pour the water from its tube into the tube containing the cysteine, then to cap and mix (e.g., by inversion or vortexing) for ~1 minute. A small amount of the resulting solution was then applied to a pad containing DTNB, and within 10-15 seconds, the application area became visibly yellow in color. Such a process is also suitable for a pad containing DTNB but no OPA as detection reagent, for example, as in a two-pad test strip.

Examples of Loci from which Sample May Be Obtained. A fluid sample for application to an apparatus such as described herein may be obtained from any of the following, provided by way of example and not of limitation: fluid expectorated or pooled (e.g., whole saliva); fluid from buccal area(s): fluid from gum line area(s); fluid from tongue dorsum. More generally, any suitable anatomical, physiological, pathophysiological and/or environmental site or locus may be contacted with a suitable collection apparatus, such as a pipet tip or a swab, in order to collect a sample for application to an apparatus such as described herein. Alternatively, a pad on an apparatus such as is described herein may be contacted directly with a fluid located at a suitable anatomical, physiological, pathophysiological and/or environmental site or locus.

Examples of Sample Delivery Methods. Delivery of sample to an apparatus as is described herein may be direct or indirect, as is suitable for a particular application. For example, a direct delivery method may be sample-to-device (expectorate onto/into device) or device-to-sample (introduce device appropriately to a specific sample site, and induce collection, for instance by touching the surface and allowing fluid to be absorbed onto/into a pad). For example, an indirect delivery method may involve a step such as expectoration into a tube, with squeezing of a sample that has been collected into the tube through a filter tip applied to a tube and thence onto or into an apparatus as is described herein; or may involve a swabbing of an oral site, for example, with a flocked swab, which collects fluid but does not retain such fluid through absorption, and delivery of the sample so collected onto or into an apparatus such as described herein.

Example of amine test (OPA-only pad) yielding fluorescent product. OPA for amine detection purposes is typically supplied as a prepared solution, containing 2-mercaptoethanol. Inclusion of thiol at a relatively high concentration assures that the OPA will react with amines, to produce fluorescent products, which can then be detected by illuminating with a UV source. For the purposes of a dry chemistry test however, using a volatile thiol would appear less feasible, since it would evaporate quickly, leaving only the 'unassisted' OPA reagent. It was found that inclusion of N-acetylcysteine at ~25-30 mM as a constituent of OPA solution (for an OPA-only dried pad) afforded the production of bright fluorescent signals for several different liquid samples (containing or consisting of, for instance putrescine, cadaverine, or whole saliva), upon illumination by a handheld UV source. Similar results were obtained (without the addition of thiol) using the reagent fluorescamine. In such cases, one would employ a non-fluorescent backing (e.g., like the blue vinyl described earlier), to minimize interference in an apparatus as is described herein.

Figure 3:
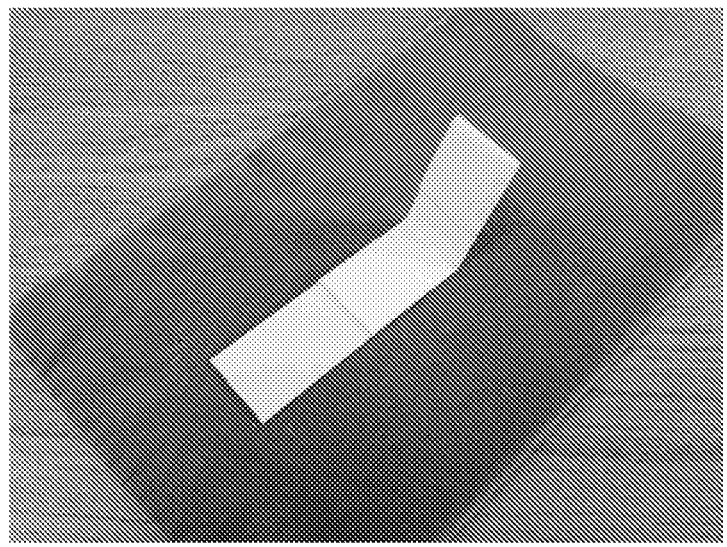
FIG. 3 depicts a test strip before it has been used.

Example Showing a "Fold-Over" Test Strip Prior to Use. FIG. 3 depicts a test strip before it has been used. An amine detection pad is on the longer section, and a thiol detection pad is situated at the top edge of the test strip. A fold has been made at notches cut into the edges of the backing, to show how the thiol pad will fold toward the amine, pad, when the sample (on a swab) is placed between the pads.

Figure 4:
FIG. 4 depicts two tests that have been used and are sitting side by side.

Examples Showing a "Fold-Over" Test Strip Subsequent to Use. FIG. 4 depicts two tests that have been used and are sitting side by side. The samples on the respective swabs were aligned over the amine pad, and the thiol pad was folded over toward the thiol pad (face to face), with the swab becoming sandwiched between the two pads. Once the swab was thusly situated, one could squeeze the folded configuration between thumb and forefinger, to help fluid absorb into the respective pads, from the stationary/sandwiched swab. In this image the device has been unfolded and the swabs have been laid across the folds of the devices. One can see the visible characteristic yellow result on the thiol pad, and the brown or gray results developed on the amine pads (here, the color on the amine pad is dependent on the pH of the OPA solution employed).

Figure 5:
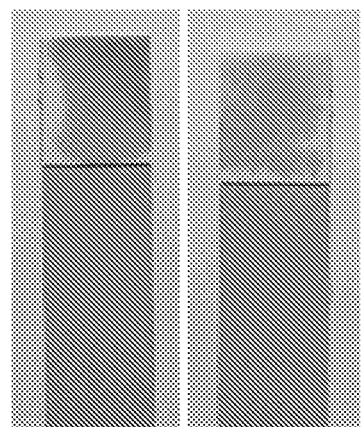
FIG. 5 depicts two tests onto each of which had been applied a tongue dorsum fluid samples, demonstrating before (left) and after (right) brushing with a dentifrice.

Examples of a "Combination Pad" Strip Containing both OPA and DTNB. FIG. 5 depicts two tests onto each of which had been applied a tongue dorsum fluid samples, demonstrating before (left) and after (right) brushing with a dentifrice. In each case, the image was recorded at 1.5 min following sample application. While there was still color in the post-brush test, the level of color was decreased relative to the pre-brush result, which was deeper brown in color and somewhat less diffuse in appearance.

Figure 6:
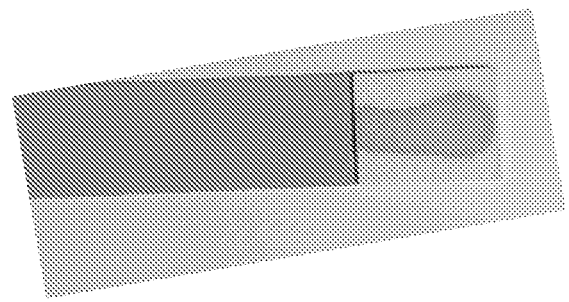
FIG. 6 depicts a result developed after applying a small amount of thiol control solution to a combination pad.

Example of a Thiol Control Applied to a "Combination Pad" Strip Containing both OPA and DTNB. FIG. 6 depicts a result developed after applying a small amount of thiol control solution to a combination pad. The color was initially yellow (e.g., through about 10-15 seconds), then became progressively brownish and 'muddier' in appearance with time.

A combination pad developed result can be regarded as a 'visible sum' of two reactions, namely the color resulting from the reaction of OPA with amines in the sample, plus the color resulting from the reaction of DTNB with thiols in the sample. It is difficult to quantify in absolute terms the quantitative contributions of amine and/or thiol to such a signal, or to estimate relative contributions of amine and thiol. An advantage this format offers is in the relative signals recorded at a given time, for situations one wishes to compare, such as before and after brushing, before and after eating/drinking a certain food/beverage, before an after a change in environmental conditions, etc.

Every reference cited herein is incorporated fully by reference. To the extent that there be any conflict between the teaching of any reference and that of the instant specification, the teaching of the instant specification shall control.

Many modifications and other embodiments will come to mind to one skilled in the art to which an apparatus such as described herein pertains having the benefit of the teachings presented in the foregoing description. Therefore, it is to be understood that the scope of rights is not to be limited to the specific embodiments disclosed and that modifications and other embodiments are intended to be included within the scope of the appended claims. Although specific terms are employed herein, they are used in a generic and descriptive sense only and not for purposes of limitation.

The illustrative Examples included herein are non-limiting Examples. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An apparatus for the simultaneous detection of amines and thiols, the apparatus comprising a thiol-detection reagent and an amine-detection reagent immobilized onto one or a plurality of pad matrices, wherein the amine-detection reagent comprises OPA or fluorescamine.

2. An apparatus for the simultaneous detection of amines and thiols, the apparatus comprising a thiol-detection reagent and an amine-detection reagent immobilized onto one or a plurality of pad matrices, wherein the amine-detection reagent comprises OPA.

3. An apparatus for the simultaneous detection of amines and thiols, the apparatus comprising a thiol-detection reagent and an amine-detection reagent immobilized onto one or a plurality of pad matrices, wherein the thiol-detection reagent comprises DTNB and the amine-detection reagent comprises OPA.

* * * * *